(12) United States Patent
Drucker (10) Patent No.: US 6,723,530 B1
(45) Date of Patent: *Apr. 20, 2004

(54) POLYNUCLEOTIDES ENCODING PROEXENDIN, AND METHODS AND USES THEREOF

(75) Inventor: Daniel J. Drucker, Ontariio (CA)

(73) Assignee: Amylin Pharmaceuticals, Inc., San Diego, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 136 days.

(21) Appl. No.: 09/019,172

(22) Filed: Feb. 5, 1998

Related U.S. Application Data (60) Provisional application No. 60/037,412, filed on Feb. 5, 1997.

(51) Int. Cl.[7] .......................... C12P 21/06; C07H 17/00; C07K 14/00
(52) U.S. Cl. .................. 435/69.1; 536/23.1; 435/320.1; 435/252.3; 435/325; 530/300; 530/350
(58) Field of Search ............................... 536/23.1, 23.5, 536/23.51, 24.3, 24.31; 530/350, 324, 326, 300; 435/69.1, 6, 91.5, 320.1, 252.3, 325

(56) References Cited

U.S. PATENT DOCUMENTS 5,424,286 A * 6/1995 Eng et al. ....................... 514/2
6,162,907 A * 12/2000 Habener ..................... 536/23.1

OTHER PUBLICATIONS

Stryer. 1981. Biochemistry, 2nd Edition, p. 629.*
Eng et al. (1992) J. Biol. Chem. 267/11, pp. 7402–05, 1992.*
Chen et al. (1997) J. Biol. Chem. 272/7, pp. 4108–4115, 1997.*
Pohl, M. and Wank, S.: "Molecular Cloning of the Helodermin and Exendin–4 cDNAs: Evidence Against the Existence of Mammalian Homologues," Gastroenterology, Supplement, vol. 112, No. 4, Apr. 1997, p. A1181 XP002066194.
Eng, et al., "Purification and Structure of Exendin–3, a New Pancreatic Secretagogue Isolated from Heloderma horridum Venom," J. Biol. Chem. 267:7402–7405 (1992).
Goke, et al., "Exendin—4 Is a High Potency Agonist–like Peptide 1–(7–39)–amide an Antagonist at the Glucagon–like Peptide 1–(7–36)–amide Receptor of Insulin–secreting β–Cells," J. Biol. Chem 268:19850–19855 (1993).
Raufman, et al., "Truncated Glucagon–like Peptide–1 Interacts with Exendin receptors on Dispersed Acini from Guinea Pig Pancreas," J. Biol. Chem 267:21432–21437 (1992).
Raufman, "Bioactive peptides from lizard venoms," Regulatory Peptides 61:1–18 (1996).
Sambrook, et al., Molecular Cloning, A Laboratory Manual, Cold Springs Harbor Press, NY (Table of Contents).

* cited by examiner

*Primary Examiner*—Karen Cochrane Carlson
(74) *Attorney, Agent, or Firm*—Arnold & Porter; David R. Marsh (57) ABSTRACT

Exendin 4 is a biologically active peptide first isolated from Gila monster venom. The invention encompasses polynucleotides encoding proexendin peptides, including exendin and novel peptides, as well as isolated or recombinant proexendin peptides. The invention also includes antibodies which specifically recognize such peptides.

62 Claims, 2 Drawing Sheets

FIGURE 1

CTGGTCTTCAGAAGTCACTGCTCAAATCTCTATTCTGAATTTGGTGCCTGTGCAAAGGAGA
AGATGAAAATCATCCTGTGGCTGTGTGTTTTGGGCTGTTCCTTGCAACTTTATTCCCTAT
CAGCTGGCAAATGCCTGTTAATCTGGGTTGTCTTCTGAGGATTCTGCAAGCTCAGAAAGC
TTTGCTTCGAAGATTAAGCGACATGGTGAAGGAACATTTACCAGTGACTTGTCAAAACAGA
TGGAAGAGGAGGCAGTGCGGTTATTTATTGAGTGGCTTAAGAACGGAGGACCAAGTAGCGG
GGCACCTCCGCCATCGGGTTAAGGTCTTTCAATTGTGGAACAAGACACACACCTGATGTTT
GATGACCATTTTAAAGAAATGTTTCCAGAAATACGTCACATGTCTTTGTTTCCAATTAGTG
AGCGACACAGCCTTTCTTAATTAAAAAATTGAAGTCATAAAAAAAAAAAAAAAAAAAAAA
AAAA

SEQUENCE LISTING

<160> NUMBER OF SEQ ID NOS: 4

<210> SEQ ID NO 1
<211> LENGTH: 492
<212> TYPE: DNA
<213> ORGANISM: LIZARD
<220> FEATURE:
<221> NAME/KEY: CDS
<222> LOCATION: (64)..(324)

<400> SEQUENCE: 1

```
ctggtcttca gaagtcactg ctcaaatctc tattctgaat ttggtgcctg tgcaaaggag      60 aag atg aaa atc atc ctg tgg ctg tgt gtt ttt ggg ctg ttc ctt gca     108
    Met Lys Ile Ile Leu Trp Leu Cys Val Phe Gly Leu Phe Leu Ala
      1               5                  10                  15 act tta ttc cct atc agc tgg caa atg cct gtt gaa tct ggg ttg tct     156
Thr Leu Phe Pro Ile Ser Trp Gln Met Pro Val Glu Ser Gly Leu Ser
                 20                  25                  30 tct gag gat tct gca agc tca gaa agc ttt gct tcg aag att aag cga     204
Ser Glu Asp Ser Ala Ser Ser Glu Ser Phe Ala Ser Lys Ile Lys Arg
             35                  40                  45 cat ggt gaa gga aca ttt acc agt gac ttg tca aaa cag atg gaa gag     252
```

```
          His Gly Glu Gly Thr Phe Thr Ser Asp Leu Ser Lys Gln Met Glu Glu
                  50                  55                  60 gag gca gtg cgg tta ttt att gag tgg ctt aag aac gga gga cca agt       300
Glu Ala Val Arg Leu Phe Ile Glu Trp Leu Lys Asn Gly Gly Pro Ser
 65                  70                  75 agc ggg gca cct ccg cca tcg ggt taaggtcttt caattgtgga acaagacaca      354
Ser Gly Ala Pro Pro Pro Ser Gly
 80                  85 cacctgatgt ttgatgacca ttttaaagaa atgtttccag aaatacgtca catgtctttg     414
tttccaatta gtgagcgaca cagcctttct taattaaaaa attgaagtca taaaaaaaaa     474
aaaaaaaaaa aaaaaaa                                                   492

<210> SEQ ID NO 2
<211> LENGTH: 87
<212> TYPE: PRT
<213> ORGANISM: LIZARD

<400> SEQUENCE: 2

Met Lys Ile Ile Leu Trp Leu Cys Val Phe Gly Leu Phe Leu Ala Thr
 1               5                  10                  15

Leu Phe Pro Ile Ser Trp Gln Met Pro Val Glu Ser Gly Leu Ser Ser
                20                  25                  30

Glu Asp Ser Ala Ser Ser Glu Ser Phe Ala Ser Lys Ile Lys Arg His
            35                  40                  45

Gly Glu Gly Thr Phe Thr Ser Asp Leu Ser Lys Gln Met Glu Glu
        50                  55                  60

Ala Val Arg Leu Phe Ile Glu Trp Leu Lys Asn Gly Gly Pro Ser Ser
 65                  70                  75                  80

Gly Ala Pro Pro Pro Ser Gly
                85

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:primer
<220> FEATURE:
<221> NAME/KEY: modified_base
<222> LOCATION: (14)
<223> OTHER INFORMATION: n=a or c or g or t
<220> FEATURE:
<221> NAME/KEY: modified_base
<222> LOCATION: (20)
<223> OTHER INFORMATION: n=a or c or g or t
<220> FEATURE:
<221> NAME/KEY: modified_base
<222> LOCATION: (23)
<223> OTHER INFORMATION: n=a or c or g or t

<400> SEQUENCE: 3
gcggaattca yggngarggn acntt                                           25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:primer
<220> FEATURE:
<221> NAME/KEY: modified_base
<222> LOCATION: (16)
<223> OTHER INFORMATION: n=a or c or g or t
```

-continued

<400> SEQUENCE: 4
cgcggatccr ttyttnarcc aytc                                                                                        24

POLYNUCLEOTIDES ENCODING PROEXENDIN, AND METHODS AND USES THEREOF

This application claims priority to Drucker, U.S. Provisional Application, Ser. No. 60/037,412, filed Feb. 5, 1997, and entitled POLYNUCLEOTIDES ENCODING PROEXENDIN AND METHODS AND USES THEREOF.

FIELD OF THE INVENTION

The invention is in the field of molecular biology. It relates, more particularly, to cloned genes and their use in diagnostic, therapeutic and related applications.

BACKGROUND TO THE INVENTION

The isolation of a novel peptide from lizard venom that displays 52% identity to mammalian GLP-1 prompted studies examining the biological properties of this protein, designated exendin 4 (Eng. et al. (1992) *J.Biol. Chem.* 267, 7402–7405). Experiments employing synthetic exendin 4 provided evidence that this peptide shares similar biological activities with mammalian GLP-1. Exendin 4 and truncated GLP-1[7–36]-amide increased cAMP levels in guinea pig acinar cell preparations (Raufman et al., 1992, *J.Biol. Chem.* 267, 21432–21437) and exendin 4 was subsequently shown to bind the GLP-1 receptor, stimulate glucose-dependent insulin secretion, and increase both cAMP accumulation and insulin gene expression in cultured islet cell lines in vitro (Goke et al., 1993, *J.Biol. Chem.* 268, 19850–19855). While full length exendin 4(1–39) is a strong agonist of GLP-1, truncated exendin 4(9–39)NH$_3$ is a competitive antagonist of both exendin 4 and GLP-1. (Raufman, 1996, *Regulatory Peptides* 61:1–18. The insulinotropic GLP-1-like properties of exendin suggest that this lizard peptide may also be useful for the treatment of patients with diabetes.

SUMMARY OF THE INVENTION

A polynucleotide coding for reptilian exendin has now been isolated and characterized. Surprisingly, the polynucleotide isolated encodes a proexendin pleiotropic peptide which encodes a novel 47 amino acid peptide fused to the amino terminus of exendin (the 47 amino acid ENTP). The first 23 amino acids of the ENTP form a consensus signal peptide sequence. At the fusion between the novel peptide and exendin is a consensus dipeptidyl peptidase cleavage site. Cleavage at this site will excise a 2mer consisting of residues 46 and 47, and exendin 4. Further, an additional glycine residue was found at the carboxyl terminus of the deduced exendin coding sequence. This additional glycine residue is presumably cleaved during post-translational processing and carboxyl terminal amidation of exendin 4.

Accordingly, the present invention provides a polynucleotide encoding a proexendin. In one embodiment, the invention provides polynucleotides encoding lizard exendin 4 peptide and a 47 amino acid exendin N-terminal peptide (47 amino acid ENTP). In a related aspect, the invention provides polynucleotides encoding a 47 amino acid ENTP. In yet a further related aspect, the invention provides a polynucleotides encoding a 23 amino acid secretory signal peptide and a 22 amino acid ENTP.

In aspects of the invention, proexendin polynucleotide or a fragment thereof are utilized for further gene cloning to identify structurally related polynucleotides and species homologs. In related aspects of the invention, anti-sense versions of proexendin encoding polynucleotide and fragments thereof are obtained and utilized to regulate proexendin expression. Accordingly, the invention also provides, in one of its aspects, polynucleotides which hybridize to the polynucleotides encoding lizard proexendin, and complements thereof. Preferably, such nucleotides hybridize under medium stringent conditions, and encode functionally equivalent gene products. In yet another aspect of the invention, there is provided polynucleotides which hybridize under stringent conditions to polynucleotides encoding lizard proexendin, and complements thereof.

In another of its aspects, the proexendin encoded peptides are provided as products of recombinant production in a cellular host. In related aspects, there are provided recombinant host cells that express proexendin cDNA, and expression constructs in which polynucleotide coding for the proexendin encoded peptides are linked to expression controls functional in the selected host cell.

In another of its aspects, substantially purified novel exendin N-terminal peptides, and substantially purified exendin 4 (1–40) are provided. In yet another of its aspects, the invention provides specific antibodies directed to the 45 amino acid or 22 amino acid ENTPs, for use for example in diagnosis of conditions wherein the level of proexendin is altered.

DETAILED DESCRIPTION AND PREFERRED EMBODIMENTS

The invention relates in one respect to polynucleotides that code for the proexendin peptides. Such polynucleotides may be in the form of RNA, or in the form of DNA including cDNA, genomic DNA and synthetic DNA.

Figure 1:
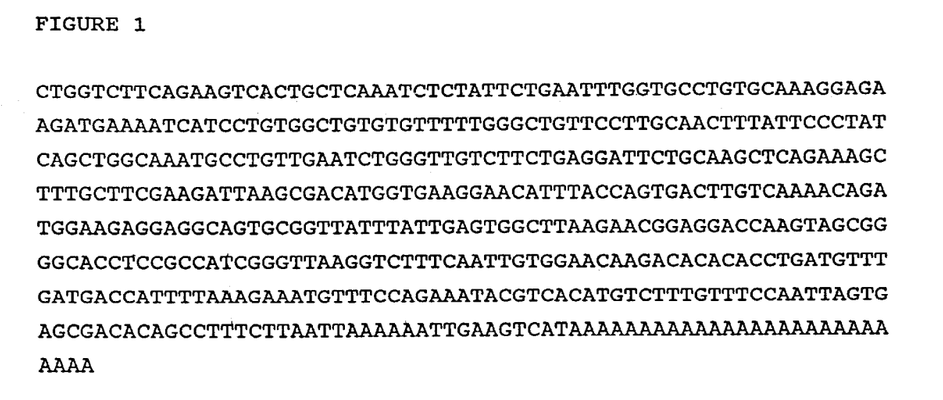
FIG. 1 is a 492 polynucleotide sequence nucleotides (SEQ ID NO:1), nucleotides 64–465 of which encode the lizard proexendin pleiotropic peptide.

In one embodiment of the invention, the proexendin transcript is encoded by nucleic acids 64–465 of the polynucleotide sequence of FIG. 1 (SEQ ID NO:1). This particular proexendin peptide encoding nucleic acid is a cDNA of lizard origin and encodes a single transcript which encodes two peptides; these are the exendin 4 peptide which it should be noted is a 40 amino acid peptide shown as amino acids 48–87 of FIG. 2 (SEQ ID NO:2), and a 45 amino acid length peptide which is shown as amino acids 1–45 amino acids of FIG. 2 (SEQ ID NO:2), linked to the N-terminus of the exendin 4 peptide by a consensus dipeptidyl peptidase cleavage site shown as amino acids 46 and 47 of FIG. 2. In addition, a consensus signal peptide sequence is found at the N-terminal end of the transcript, indicating that the two encoded peptides are secreted from the cell. Thus, it seems the 45 amino acid ENTP peptide includes a 23 amino acid signal peptide sequence, and a 22 amino acid ENTP. By analogy with other polynucleotide sequences encoding peptide hormones, such as glucagon and calcitonin, the ENTP peptide is expected to exhibit biological activity as a peptide hormone.

The invention is also based, in part, on the discovery that mammalian homologs of proexendin exist. As shown by way of working examples, below, such homologs are at least expressed in murine heart, skeletal muscle, and pancreas. Given this information, as well as the demonstrated biological activities of exendin 4 on a variety of different mammalian cells, (including human, guinea pig and rat) homologs of proexendin are likely to be found in all mammalian species.

The proexendin nucleotide sequences of the invention include: (a) the DNA sequence shown in FIG. 1 (SEQ ID NO:1); (b) the nucleotide sequence that encodes the amino acid sequence shown in FIG. 2 (SEQ ID NO:2); (c) any nucleotide sequence that hybridizes to the complement of the DNA sequence shown in FIG. 1 (SEQ ID NO:2) under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/ 0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and (d) any nucleotide sequence that hybridizes to the complement of the DNA sequences that encode the amino acid sequence shown in FIG. 2 under less stringent conditions, such as moderately stringent conditions, e.g., washing in 0.2×SSC/0.1% SDS at 42° C. (Ausubel et al., 1989, supra), yet which still encodes a functionally equivalent gene product. Functional equivalents of the proexendin include naturally occurring proexendin present in other species, and mutant proexendin whether naturally occurring or engineered which retain at least some of the functional activities of proexendin (i.e., processing to peptides ENTP and exendin, binding to the exendin receptor, agonist of GLP-1, stimulate adenylate cyclase production, antagonist of GLP-1). The invention also includes degenerate variants of sequences (a) through (d).

The invention also includes nucleic acid molecules, preferably DNA molecules, that hybridize to, and are therefore the complements of, the nucleotide sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/ 0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as proexendin antisense molecules, useful, for example, in proexendin gene regulation (for and/or as antisense primers in amplification reactions of proexendin gene nucleic acid sequences). With respect to proexendin gene regulation, such techniques can be used to regulate, for example, suppression of cell function. Further, such sequences may be used as part of ribozyme and/or triple helix sequences, also useful for proexendin gene regulation. Still further, such molecules may be used as components of diagnostic methods whereby, for example, the tissue type of a tumor cell may be determined.

In addition to the proexendin nucleotide sequences described above, full length proexendin cDNA or gene sequences present in the same species and/or homologs of the proexendin gene transcripts present in other species can be identified and readily isolated, without undue experimentation, by molecular biological techniques well known in the art. As shown below by way of example, the proexendin transcript is conserved between mammalian and reptilian species. Indeed, polynucleotides encoding homologs of novel proexendin may be isolated from a variety of mammalian cells, preferably human and murine cells, known or suspected to contain proexendin, particularly cells of salivary gland, skeletal muscle, heart, and pancreatic origin.

In one embodiment the invention provides proexendin polynucleotide, or fragments thereof, as a tools useful to identify structurally related nucleic acids. At low stringency hybridization conditions, for instance, nucleic acid libraries can be probed to identify genes that are at least about 40% homologous to the proexendin gene. Obviously, if the homolog from a particular species is sought e.g. human, the appropriate library should be probed. To facilitate isolation of exendin encoding homologs of the lizard exendin gene, homologs desirably have 80% sequence identity at the nucleic acid level to the lizard exendin gene. More desirably they are 90% identical, and most desirably they have at least 95% sequence identity when compared to the lizard proexendin gene. It will be clear that increasing the stringency of the hybridization conditions will result in increased sequence identity of the homolog thereby isolated, with lizard exendin gene. For example, the nucleic acids of the present invention may be used to isolate the exendin 3 gene by probing, using high stringency conditions, a cDNA library derived from the salivary gland of the lizard *Heloderma horridum*. In order to isolate exendin encoding homologs of the lizard proexendin gene it is desirable but not essential to screen libraries of pancreas, heart or skeletal muscle origin. Therefore, the invention includes not only lizard exendin encoding genes but structural homologs and particularly those that code for proteins having exendin like properties e.g. bind to the GLP-1 receptor. Thus, the invention provides polynucleotides that encode proexendin, including lizard proexendin genes, reptilian proexendin genes, and mammalian homologs thereof.

The identification of homologs of the novel proexendin in related species can be useful for developing animal model systems more closely related to humans for purposes of drug discovery. For example, cDNA libraries, or genomic DNA libraries derived from the organism of interest can be screened by hybridization using the nucleotides described herein as hybridization or amplification probes. Furthermore, genes at other genetic loci within the genome that encode proteins which have extensive homology to one or more novel domains of the proexendin gene product can also be identified via similar techniques. In the case of cDNA libraries, such screening techniques can identify clones derived from alternatively spliced transcripts in the same or different species.

It will be apparent to the skilled worker that sequences of the exendin gene of at least about 15 nucleotides, and preferably of at least about 17 nucleic acids, could be used to generate probes useful to identify nucleic acid molecules encoding proexendin homologs. These sequences, and the intact gene itself, may be used of course to clone proexendin related genes by standard hybridization techniques. For example, DNA coding for other exendins, for example other lizard exendins or mammalian homologs, can be obtained by applying selected techniques of gene isolation or gene synthesis. Screening can be by filter hybridization, using duplicate filters. The labeled probe can contain at least 15–30 base pairs of the proexendin nucleotide sequence, as shown in FIG. 1. The hybridization washing conditions used should be of a lower stringency when the cDNA library is derived from an organism different from the type of organism from which the labeled sequence was derived. With respect to the cloning of a murine homolog of proexendin, using reptilian proexendin probes, hybridization can, for example, be performed at 50° C. overnight (in 1% SDS, 1 M NaCl, 2 µM EDTA, 1% BSA). Washes can be done with 0.1×SSC, 1% SDS at 50° C. With respect to the cloning of a human homolog of the novel proexendin, using murine proexendin probes, hybridization can, for example, be performed at 65° C. overnight in Church's buffer (7% SDS, 250 mM NaHPO$_4$, 2 µM EDTA, 1% BSA). Washes can be done with 2×SSC, 0.1% SDS at 65° C. and then at 0.1×SSC, 0.1% SDS at 65° C. Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Isolation of the exendin homolog typically will entail extraction of total messenger RNA from a fresh source of pancreas, heart or skeletal muscle tissue, followed by conversion of message to cDNA and formation of a library in for example a bacterial plasmid, more typically a bacteriophage. Such bacteriophage harboring fragments of the human DNA are typically grown by plating on a lawn of susceptible *E. coli* bacteria, such that individual phage plaques or colonies can be isolated. The DNA carried by the phage colony is then typically immobilized on a nitro-cellulose or nylon-based hybridization membrane, and then hybridized, under carefully controlled conditions, to a radioactively (or otherwise) labelled probe sequence to identify the particular phage colony carrying the fragment of DNA of particular interest, in this case a proexendin homolog. The phage carrying the particular gene of interest is then purified away from all other phages from the library, in order that the foreign gene may be more easily characterized. Typically, the gene or a portion thereof is subcloned into a plasmidic vector for convenience, especially with respect to the full determination of its DNA sequence. Therefore, having herein provided the lizard proexendin gene, it will be appreciated by one of ordinary skill in the art of molecular biology mammalian homologs of the lizard exendin gene are available by screening mammalian pancreas, heart or skeletal muscle cDNA or genomic library by using the lizard exendin gene or fragments thereof as a probe, using standard molecular biological techniques.

Further, a proexendin gene homolog may be isolated from nucleic acid of the organism of interest by performing PCR using two degenerate oligonucleotide primer pools designed on the basis of amino acid sequences within the novel proexendin gene product disclosed herein. The template for the reaction may be cDNA obtained by reverse transcription of mRNA prepared from, for example, human or non-human cell lines or cell types, such as heart, skeletal muscle, and pancreas cell types, known or suspected to express such a proexendin gene allele.

The invention also encompasses nucleotide sequences that encode mutant proexendin, peptide fragments of proexendin, truncated proexendin protein, and proexendin fusion proteins. Particularly preferred polynucleotides are those which encode functional domains of proexendin, such as the 47 amino acid ENTP peptide, the 45 amino acid ENTP peptide, the deduced 23 amino acid secretory signal, the 22 amino acid ENTP peptide, and the exendin peptides 1–40, 1–39 and 9–39. Nucleotides encoding fusion proteins may include but are not limited to full length proexendin, truncated proexendin, or peptide fragments of proexendin fused to an unrelated protein or peptide, such as for example, an epitope tag which aids in purification or detection of the resulting fusion protein; or an enzyme, fluorescent protein, luminescent protein which can be used as a marker.

The proexendin gene sequences may additionally be used to isolate mutant proexendin gene alleles. Such mutant alleles may be isolated from individuals either known or proposed to have a genotype which contributes to the symptoms of metabolic abnormalities. Additionally, such proexendin gene sequences can be used to detect proexendin gene regulatory (e.g., promoter or promotor/enhancer) defects which may be involved in metabolic disorders. Further, nucleotides encoding the deduced secretory signal sequence may be fused in frame to nucleotides encoding heterologous gene products and thus used to direct the secretion of such gene products.

The invention also encompasses (a) DNA vectors that contain any of the foregoing proexendin coding sequences and/or their complements (i.e., antisense); (b) DNA expression vectors that contain any of the foregoing proexendin coding sequences operatively associated with a regulatory element that directs the expression of the coding sequences; and (c) genetically engineered host cells that contain any of the foregoing proexendin coding sequences operatively associated with a regulatory element that directs the expression of the coding sequences in the host cell.

Having proexendin encoding nucleic acid in hand, the proexendin gene products can be produced in a number of ways, including in vitro transcription and via incorporation of the DNA into a suitable expression vector and expression in the appropriate host, for example a bacteria such as *E. coli*, yeast or a mammalian cell. It should be noted that a material is said to 'isolated' or 'substantially free of natural contaminants' if it has been substantially purified from materials with which it is normally and naturally found. It should be noted that the term 'recombinant polynucleotide' as used herein means that the polynucleotide is not in its natural environment, for example the polynucleotide is functionally associated with heterologous nucleic acid sequences. A variety of gene expression systems have been adapted for use with these hosts and are now commercially available, and any one of these systems can be selected to drive expression of the exendin-encoding DNA. Expression vectors may be selected to provide transformed cell lines that express the proexendin-encoding DNA either transiently or in a stable manner. For transient expression, host cells are typically transformed with an expression vector harboring an origin of replication functional in a mammalian cell. For stable expression, such replication origins are unnecessary, but the vectors will typically harbor a gene coding for a product that confers on the transformants a survival advantage, to enable their selection such as a gene coding for neomycin resistance in which case the transformants are plated in medium supplemented with neomycin.

These systems, available typically in the form of plasmidic vectors, incorporate expression cassettes the functional components of which include DNA constituting expression controlling sequences, which are host-recognized and enable expression of the proexendin-encoding DNA when linked 5' thereof. The systems further incorporate DNA sequences which terminate expression when linked 3' of the proexendin-encoding region. Thus, for expression in the selected mammalian cell host, there is generated a recombinant DNA expression construct in which the proexendin-encoding DNA is linked with expression controlling DNA sequences recognized by the host, and which include a region 5' of the proexendin-encoding DNA to drive expression, and a 3' region to terminate expression.

Included among the various recombinant DNA expression systems that can be used to achieve mammalian cell expression of the exendin encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals i.e., the metallothionein gene promoter, and other steroid-inducible promoters.

Novel proexendin polypeptides and peptide fragments, mutated, truncated or deleted forms of proexendin and proexendin fusion proteins can be prepared for a variety of uses, including but not limited to the generation of antibodies, as reagents in diagnostic assays, the identification of other cellular gene products involved in the regulation of cellular metabolism, as reagents in assays screening for compounds that can be used in the treatment of metabolism disorders, and as pharmaceutical reagents useful in the treatment of metabolic disorders such as diabetes.

Figure 2:
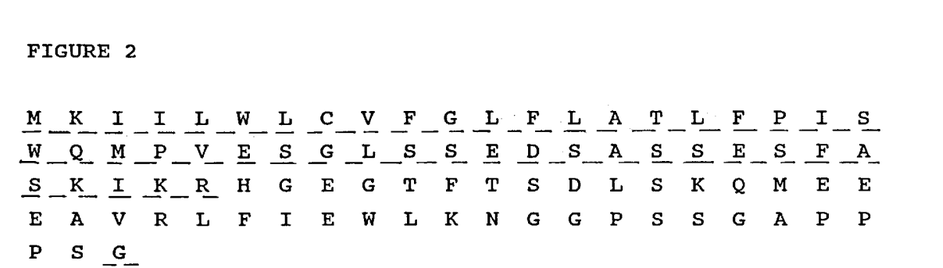
FIG. 2 is the 87 amino acid sequence of the lizard proexendin gene product (SEQ ID NO:2). The broken lines underscore the novel ENTP sequence, and the carboxyl terminal region of proexendin which diverges from the published sequences of exendin proteins.

The proexendin amino acid sequences of the invention include the amino acid sequence shown in FIG. 2 (SEQ ID No:2). Further, proexendins of other species are encompassed by the invention. In fact, any protein encoded by the proexendin nucleotide sequences described above, as long as they contain either the ENTP sequence or the novel carboxyl terminus of exendin, are within the scope of the invention.

For use particularly in detecting the presence and/or location of exendin and the ENTPs, for example in venom, pancreas, heart or skeletal muscle cells, the present invention also provides, in another of its aspects, antibody to the ENTP peptides or to exendin. Antibodies to proexendin peptide sequences, including antibodies specific for domains of proexendin, are useful for a variety of purposes. For example, proexendin, including the ENTP peptides, may be used as a marker for tissue specific activity. Endocrine tumors which secrete abnormal amounts of proexendin, or fragments of proexendin, may be detected by assaying for the circulating levels of proexendin or proexendin fragments. Specifically, proexendin is known to be expressed by pancreas, heart, and skeletal muscle tissue. Further, organ or tissue failure of proexendin-expressing tissues may be revealed by an alteration or decrease in the amount of detectable proexendin. Additionally, such antibodies are useful in detecting the presence and level of venom peptides in humans suffering from envenomation following reptilian bites. Moreover, such antibodies are useful for neutralizing venom proteins.

To raise such antibodies the ENTP gene product or exendin or immunogenic fragments thereof may be used, produced in a microbial or mammalian cell host as described above or by standard peptide synthesis techniques. Specifically, the 45 amino acid ENTP or the 22 amino acid ENTP or immunogenic fragments thereof may be used in this. Standard immunization protocols may be followed. Typically, the peptides would be formulated in PBS, or an adjuvant such as Freunds or alum may be incorporated in the immunogen. Usually for peptides less than 10 kd in molecular weight the peptide is conjugated to a carrier such as Keyhole Limpet hemocyanin. In one useful immunization protocol the test animals would typically be injected subcutaneously with immunogen having in the order of 0.5–1 mg of the peptide per bolus followed by a intramuscular booster injection approximately 2 to 3 weeks later with 100–200 µg of peptide formulated in PBS. The intramuscular injection may be repeated 2–3 weeks later if test bleeds show it to be required.

One source of antibodies to the desired proexendin gene products or fragment thereof is from the blood of an animal that has been immunized with the above mentioned immunogens. Alternatively, for monoclonal antibody production, immunocytes such as splenocytes can be recovered from the immunized animal and fused, using hybridoma technology, to myeloma cells. Monoclonal antibodies are particularly preferred for generating antibodies specific to a single epitope. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

Animal model systems which elucidate the physiological and behavioral roles of the proexendin gene products are produced by creating transgenic animals in which the activity of the peptide encoded therein are either increased or decreased, or the amino acid sequence of the expressed proexendin peptide of interest is altered, by a variety of techniques. Examples of these techniques include, but are not limited to: 1) insertion of normal or mutant versions of DNA encoding proexendin peptides, by microinjection, electroporation, retroviral transfection or other means well known to those skilled in the art, into appropriate fertilized embryos in order to produce a transgenic animal, or 2) homologous recombination of mutant or normal, human or animal versions of these genes with the native gene locus in transgenic animals to alter the regulation of expression or the structure of these peptide sequences. The technique of homologous recombination is well known in the art. It replaces the native gene with the inserted gene and so is useful for producing an animal that cannot express native proexendin peptides but does express, for example, an inserted mutant proexendin peptides, which have replaced the native proexendin peptides in the animals genome by recombination, resulting in underexpression of the peptides. Microinjection adds genes to the genome, but does not remove them, and so is useful for producing an animal which expresses its own and added proexendin peptides, resulting in overexpression of the proexendin or peptides of interest.

One means available for producing a transgenic animal, with a mouse as an example, is as follows. Female mice are mated, and the resulting fertilized eggs dissected out of their oviducts. The eggs are stored in an appropriate medium such as M2 medium. A vector containing DNA or cDNA encoding a proexendin peptide is cesium chloride purified from by methods well known in the art. Inducible promoters may be fused with the coding region of the DNA to provide an experimental means to regulate expression of the transgene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy, but which is not actually pregnant), where it proceeds to the uterus, implants, and develops to term. As noted above, microinjection is not the only methods for inserting DNA into the egg cell, and is used here only for exemplification purposes.

EXAMPLE 1

Isolation of the Proexendin Gene

Total cellular RNA from lizard Heloderma suspectum salivary gland was isolated by the acid guanidium thiocyanate method (Chomczynski, P. et al., 1987, *Anal. Chem.* 169, 158–159). For first strand cDNA synthesis, 5 μg total cellular RNA was reverse-transcribed using SuperScript Preamplification system (Gibco-Bethesda Research Laboratories (BRL), Gaithersburg, Md.). An aliquot of the first strand cDNA (0.1 vol) was subsequently amplified by PCR (35 cycles, annealing temperature of 50° C., extension temperature of 72° C.). For isolation of lizard exendin, the degenerate primers were LE(A); 5'-GCG GAA TTC AYG GNG ARG GNA CNTT-3' (SEQ ID NO:3), and LE(B), 5'-CGC GGA TCC RTT YTT NAR CCA YTC-3' (SEQ ID NO:4). Amplification products were cloned into the TA cloning vector pCRII from Invitrogen (San Diego, Calif.) and sequenced. RNA from lizard salivary gland generated a PCR product of the predicted size (95 bp), and sequencing of this partial cDNA demonstrated that it encoded the sequence of exendin 4. To isolate a full length exendin cDNA, a lizard salivary gland cDNA library was prepared and then screened with the partial exendin cDNA probe. An *H. suspectum* cDNA library was made from poly (A)+ mRNAs isolated from the salivary glands of an adult lizard, consisting of 1×10⁶ independent recombinant phagemid was constructed in the EcoRI sites of the pcDNA II vector (Invitrogen, San Diego, Calif.). The cDNA library was screened with the above 95 bp nucleotide sequence EcoRI/BamHI [α32P]-dATP labelled lizard cDNA generated by RT-PCR as described directly above. A single class of exendin cDNA clones was isolated from the library that encoded exendin (amino acids 48–87 of FIG. 1) and a 45 amino acid peptide (amino acids 1–45 of FIG. 1) N-terminal to the exendin sequence, designated exendin N-terminal peptide (ENTP). The ENTP sequence is followed by a dibasic pair of amino acids, lysine and arginine, characteristic of prohormone convertase cleavage sites, and the 40 amino acid exendin sequence.

EXAMPLE 2

Identification of Mammalian Homologs of Exendin

The lizard exendin nucleotide probe can be used to obtain mammalian exendin cDNAs by standard molecular biology techniques. In this example, the lizard exendin probe was ³²P-labelled by the random priming technique, and used in Northern blot analysis (hybridization was performed at 50° C. in 1M NaCl, 1% SDS and washing was performed at 50° C. in 0.1×SSC, 1% SDS) to detect corresponding mouse exendin mRNA transcripts in various mouse tissues. Mouse exendin mRNA transcripts, about 1.2 kb in size, were detected in RNA from mouse heart. Mouse exendin mRNAs were also detected, about 1.0 kb in size, in RNA from skeletal muscle, and a mouse exendin RNA transcript of about 1.0 kb can be detected in RNA from mouse pancreas. To those skilled in the art, mouse exendin cDNAs, as well as other mammalian exendin cDNAs, containing the full length nucleotide mammalian exendin cDNA can be obtained from these tissues by screening cDNA libraries with the lizard exendin probe, or by the use of RT-PCR.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying figures. Such modifications are intended to fall within the scope of the appended claims.

What is claimed is:

1. An isolated polynucleotide comprising a nucleotide that encodes a proexendin, wherein said proexendin comprises a signal sequence, a pro-hormone N-terminal sequence, and an amino acid sequence encoding a naturally occurring mature exendin comprising 39 amino acids, wherein the mature form of said proexendin has the ability to bind to and activate the pancreatic GLP-1 receptor, stimulate glucose-dependent insulin secretion, or increase both cAMP accumulation and insulin gene expression in islet cells, and complements thereof.

2. The isolated polynucleotide of claim 1, wherein the proexendin comprises at least 80% sequence identity to the amino acid sequence SEQ ID NO: 2.

3. The isolated polynucleotide of claim 2, wherein the proexendin comprises at least 90% sequence identity to the amino acid sequence SEQ ID NO: 2.

4. The isolated polynucleotide of claim 3, wherein the proexendin comprises at least 95% sequence identity to the amino acid sequence SEQ ID NO: 2.

5. The polynucleotides of claim 1, wherein said polynucleotide comprises a nucleotide sequence that encodes a polypeptide comprising amino acids 48 to of SEQ ID NO: 2.

6. The polynucleotide of claim 5, wherein the polynucleotide comprises nucleotides 205 to 324 of SEQ ID NO: 1.

7. The polynucleotide of claim 1, wherein said polynucleotide comprises a nucleotide sequence that encodes the amino acid sequence SEQ ID NO: 2.

8. The polynucleotide of claim 7, wherein the polynucleotide comprises nucleotides 64 to 324 of SEQ ID NO: 1.

9. The polynucleotide of claim 1, wherein said polynucleotide is a cDNA polynucleotide.

10. The polynucleotide of claim 1, wherein said polynucleotides is a synthetic polynucleotide.

11. An isolated polynucleotide encoding amino acids 1 to 47, 1 to 45, 1 to 23, 24 to 47, 24 to 45, or 48 to 87 of SEQ ID NO: 2, and complements thereof.

12. The polynucleotide of claim 11, wherein said polynucleotide encodes amino acids 1 to 47 of SEQ ID NO: 2.

13. The polynucleotide of claim 12, wherein said polynucleotide comprises nucleotides 64 to 204 of SEQ ID NO: 1.

14. The polynucleotide of claim 11, wherein said polynucleotide encodes amino acids 1 to 45 of SEQ ID NO: 2.

15. The polynucleotide of claim 14, wherein said polynucleotide comprises nucleotides 64 to 198 of SEQ ID NO: 1.

16. The polynucleotide of claim 11, wherein said polynucleotide encodes amino acids 1 to 23 of SEQ ID NO: 2.

17. The polynucleotide of claim 16, wherein said polynucleotide comprises nucleotides 64 to 132 of SEQ ID NO: 1.

18. The polynucleotide of claim 11 wherein said polynucleotide encodes amino acids 24–47 of SEQ ID NO: 2.

19. The polynucleotide of claim 18, wherein said polynucleotide comprises nucleotides 133 to 204 of SEQ ID NO: 1.

20. An isolated polynucleotide of claim 11, wherein said polynucleotide encodes amino acids 24–45 of SEQ ID NO: 2.

21. The polynucleotide of claim 20, wherein said polynucleotide comprises nucleotides 133 to 198 of SEQ ID NO: 1.

22. An isolated polynucleotide of claim 11, wherein said polynucleotide encodes amino acids 48–87 of SEQ ID NO: 2.

23. The polynucleotide of claim 22, wherein said polynucleotide comprises nucleotides 205–324 of SEQ ID NO: 1.

24. An isolated polynucleotide of claim 11, wherein the polynucleotide further comprises a polynucleotide encoding an epitope tag or a marker.

25. An isolated polynucleotide of claim 24, wherein the marker is an enzyme, a fluorescent protein, or a luminescent protein.

26. An isolated fragment comprising at least 15 consecutive nucleotides of nucleotides 64–324 of SEQ ID NO: 1, wherein said fragment encodes a polypeptide has the ability to bind to and activate the pancreatic GLP-1 receptor, stimulate glucose-dependent insulin secretion, or increase both cAMP accumulation and insulin gene expression in islet cells.

27. An isolated fragment comprising at least 15 consecutive nucleotides of the nucleotide 64 to 324 of SEQ ID NO: 1, wherein said fragment encodes a polypeptide capable of being processed to peptides exendin N-terminal peptide (ENTP) and exendin, binding to the exendin receptor, acting as an agonist or antagonist of GLP-1, or stimulating adenylate cyclase production, and complements thereof.

28. The polynucleotides of claim 27, wherein said fragment encodes a polypeptide comprising amino acids 56–86 of SEQ ID NO: 2, and complements thereof.

29. An isolated polynucleotide that hybridizes under stringent conditions with the complement of a polynucleotide encoding SEQ ID NO: 2, wherein said stringent conditions are hybridizing in 0.5 M $NaHPO_4$, 7% sodium dodecyl sulfate (SDS), 1 nM EDTA, at 65° C. and washing in 0.1×SSC/0.1% SDS at 68° C., wherein the polynucleotide encodes a pro-polypeptide which in its mature form is a polypeptide that has the ability to bind to and activate the pancreatic GLP-1 receptor, stimulate glucose-dependent insulin secretion, or increase both cAMP accumulation and insulin gene expression in islet cells, wherein the polynucleotide does not encode GLP-1, and complements thereof.

30. The polynucleotide of claim 29, wherein the wash condition is 6×SSC/0.05% sodium pyrophosphate at 37° C.

31. An isolated polynucleotide according to claim 29 wherein said polynucleotide is derived from the lizard *Heloderma horridum*.

32. An isolated polynucleotide which hybridizes under moderately stringent conditions with the complement of the polynucleotide encoding SEQ ID NO: 2, wherein said moderately stringent conditions are hybridizing in 0.5 M NaHPO4, 7% SDS, 1 nM EDTA, at 65° C. and washing in 0.2×SSC/0.1% SDS at 42° C., wherein the polynucleotide encodes a pro-polypeptide which in its mature form is a polypeptide that has the ability to bind to and activate the pancreatic GLP-1 receptor, stimulate glucose-dependent insulin secretion, or increase both cAMP accumulation and insulin gene expression in islet cells, and wherein the polynucleotide does not encode GLP-1, and complements thereof.

33. An isolated polynucleotide according to claim 32 wherein said polynucleotide is derived from the lizard Heloderma horridum.

34. An isolated polynucleotide that hybridizes under low stringency conditions with the complement of a polynucleotides encoding SEQ ID NO: 2, wherein said conditions are hybridizing in 1% SDS, 1 M NaCl, 2 $\mu$M EDTA, and 1% BSA at 50° C. and washing in 0.1×SSC/1% SDS at 50° C., wherein the polynucleotide encodes a pro-polypeptide which in its mature form is a polypeptide, that has the ability to bind to and activate the pancreatic GLP-1 receptor in vitro, and wherein the polynucleotide does not encode GLP-1, and complements thereof.

35. An isolated polynucleotide according to claim 34 wherein said polynucleotide is derived from the lizard Heloderma horridum.

36. An expression vector comprising the polynucleotide of claim 1.

37. A host cell comprising the vector of claim 36.

38. A method for producing exendin, said method comprising culturing the host cell of claim 37 under conditions which express proexendin, and isolating exendin from the culture media.

39. An expression vector comprising the polynucleotide of claim 7.

40. A host cell comprising the vector of claim 39.

41. A method for producing exendin, said method comprising culturing the host cell of claim 40 under conditions which express proexendin, and isolating exendin from the culture media.

42. An expression vector comprising the polynucleotide of claim 11.

43. A host cell comprising the vector of claim 42.

44. A method for producing exendin, said method comprising culturing the host cell of claim 43 under conditions which express proexendin, and isolating exendin from the culture media.

45. An expression vector comprising the polynucleotide of claim 20.

46. A host cell comprising the vector of claim 45.

47. A method,for producing exendin, said method comprising culturing the host cell of claim 46 under conditions which express proexendin, and isolating exendin from the culture media.

48. An expression vector comprising the polynucleotide of claim 32.

49. A host cell comprising the vector of claim 48.

50. A method for producing exendin, said method comprising culturing the host cell of claim 49 under conditions which express proexendin, and isolating exendin from the culture media.

51. An expression vector comprising the polynucleotide of claim 34.

52. A host cell comprising the vector of claim 51.

53. A method for producing exendin, said method comprising culturing the host cell of claim 52 under conditions which express proexendin, and isolating exendin from the culture media.

54. An isolated polynucleotide comprising at least 80% identity to nucleotides 205 to 321 of SEQ ID NO: 1, wherein said polynucleotide encodes an exendin polypeptide having the ability to bind to and activate the pancreatic GLP-1 receptor, stimulate glucose-dependent insulin secretion, or increase both cAMP accumulation and insulin gene expression in islet cells, and complements thereof.

55. The isolated polynucleotide of claim 54, wherein the polynucleotide comprises at least 90% sequence identity to nucleotides 205 to 321 of SEQ ID NO: 1.

56. The isolated polynucleotide of claim 55, wherein the polynucleotide comprises at least 95% sequence identity to nucleotides 205 to 321 of SEQ ID NO: 1.

57. The isolated polynucleotide of claim 56, wherein the polynucleotide comprises nucleotides 205 to 321 of SEQ ID NO: 1.

58. An isolated polynucleotide of claim 54, wherein the polynucleotide further comprises a polynucleotide encoding an epitope tag or a marker.

59. An isolated polynucleotide of claim 58, wherein the marker is an enzyme, a fluorescent protein, or a luminescent protein.

60. An expression vector comprising the polynucleotide of claim 54.

61. A host cell comprising the vector of claim 60.

62. A method for producing exendin, said method comprising culturing the host cell of claim 61 under conditions which express proexendin, and isolating exendin from the culture media.

\* \* \* \* \*

UNITED STATES PATENT AND TRADEMARK OFFICE
CERTIFICATE OF CORRECTION

PATENT NO. : 6,723,530 B1  Page 1 of 1
APPLICATION NO. : 09/019172
DATED : April 20, 2004
INVENTOR(S) : Daniel J. Drucker It is certified that error appears in the above-identified patent and that said Letters Patent is hereby corrected as shown below:

Col. 13 Claim 5, Line 3, change "48 to of" to correctly recite -- 48 to 87 of --

Signed and Sealed this

Twenty-ninth Day of January, 2008

JON W. DUDAS
*Director of the United States Patent and Trademark Office*